United States Patent [19]

Herrick

[11] 4,124,303
[45] Nov. 7, 1978

[54] SURFACE-GLOSS MEASURING DEVICE
[75] Inventor: Burkett C. Herrick, Bloomfield Hills, Mich.
[73] Assignee: Tuff-Kote Dinol, Inc., Warren, Mich.
[21] Appl. No.: 784,718
[22] Filed: Apr. 5, 1977
[51] Int. Cl.² ............................................. G01N 21/48
[52] U.S. Cl. .................................................... 356/445
[58] Field of Search ................................. 356/209, 210
[56] References Cited
U.S. PATENT DOCUMENTS
2,830,490  4/1958  Pellegrini ............................. 356/210
FOREIGN PATENT DOCUMENTS
686,941  1/1940  Fed. Rep. of Germany ........... 356/209
OTHER PUBLICATIONS
Henry A. Gardner Laboratory, Inc. "Instruments and Methods for Determining Gloss, Surface Texture Sharpness of Reflected Images and Bloom", Mar. 1936.

Primary Examiner—John K. Corbin
Assistant Examiner—R. A. Rosenberger
Attorney, Agent, or Firm—Dayton R. Stemple, Jr.

[57] ABSTRACT

An elongated cylinder having a hollow interior is provided with a first open end and a second closed end. Reflecting media are provided on the interior portion of the closed end and on half of the inner surface of the circumferential wall surface of the cylinder. First and second scales are provided on the other half of the wall surface, each being translucent in part so that incident light directed into the interior of the elongated cylinder will pass therethrough. The gloss of a surface may be measured by placing the closed end of the elongated cylinder on the surface and directing an incident light into the hollow interior via the first open end, and noting the reflection of the scales in the surface being measured. The glossier the surface, the more of the scales that will be reflected.

8 Claims, 3 Drawing Figures

SURFACE-GLOSS MEASURING DEVICE

BACKGROUND OF THE INVENTION

The present invention is directed to a device for visually measuring the gloss of a surface, and particularly the gloss of the surface of an automobile, so that comparisons may be made between the polishing effectiveness of different polishing chemicals.

There are many known devices for measuring specific qualities of a surface. For example, in U.S. Pat. No. 3,396,627 there is disclosed a device for measuring surface roughness, while in U.S. Pat. No. 3,349,665 there is disclosed a device for measuring the reflecting properties of a surface. Both of these prior art devices, however, are costly to produce and require a much greater degree of technological sophistication than the present invention which is designed for easy use by anyone desiring to approximately gauge the differences in gloss of surfaces.

U.S. Pat. No. 2,799,203 also discloses a device for visually measuring the characteristics of a glossy surface, but which is cumbersome to use and costly to produce.

SUMMARY OF THE INVENTION

It is, therefore, an object of the present invention to provide a device for measuring the gloss of a surface, and particularly the gloss of an automobile surface in a manner that is quick and simple to use.

It is another object of the present invention to provide such a device that is relatively inexpensive to produce.

Briefly, the present invention contemplates an elongated cylinder having a hollow interior, one end of which is closed off by a reflecting medium, such as aluminum foil. The other end of the elongated cylinder is open so that the bulb-end of a conventional flashlight may be placed thereon. The cylinder itself is mostly black and made of a translucent material, such as Lucite, with one-half of the interior circumferential wall surface of the cylinder being covered with a reflecting medium, such as aluminum foil. The other half of the circumferential wall surface of the elongated cylinder is provided with a pair of scales, one scale being white on a field of black, while the other scale is black on a field of white, so that depending upon the color of the surface to be measured one or the other of the scales is used.

When using the device of the invention, the bulb-end of a conventional flashlight is placed on the open end of the elongated cylinder, while the other, closed end of the elongated cylinder is placed on top of the surface whose gloss is to be visually measured. Thereupon, the flashlight is turned on so that the light emanating therefrom passes only through the white translucent part of the elongated cylinder forming part of the two scales therein. The reflective medium on the closed end and on the half of the interior circumferential wall surface of the elongated cylinder reflects the incident light from the flashlight through the white translucent part. Depending upon the gloss of the surface being measured, a reflection of the scales will result in the glossy surface. The reflection will indicate the degree of polish of the surface via the portion of the scales that are reflected thereby. For a very glossy surface, most or all of a scale will be reflected, so that, for example, the scale reference 500 will be able to be read in the reflection. On another, less glossy surface, only the scale reference 250, for example, will be able to be read in the reflection, indicating a relatively less glossy surface compared to the one reflecting the scale reference 500.

The invention has special relevance in comparing the degree of finish of a polishing agent, where, before the polish is applied to the surface, the reflection of the scales would indicate a certain number, and after the polish was applied the reflection would indicate another higher number. Polishing agents may be compared by comparing the highest numbers reflected in the surfaces using different polishing agents.

BRIEF DESCRIPTION OF THE DRAWING

The invention will be more readily understood with reference to the following detailed description, when taken in conjunction with the accompanying drawing, wherein.

DETAILED DESCRIPTION OF THE INVENTION

Figure 2:
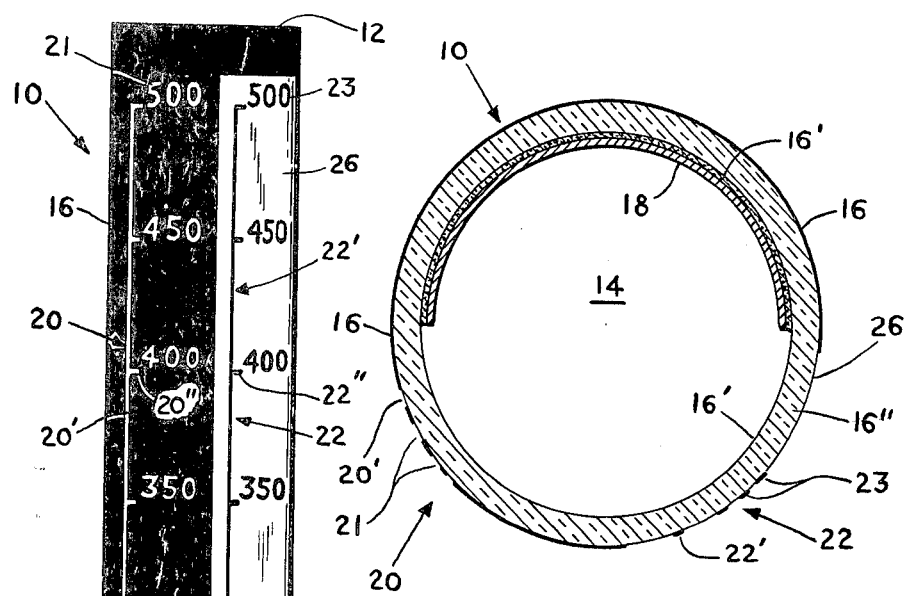
FIG. 2 is a cross-sectional view taken along line 2—2 of FIG. 1.
Figure 1:
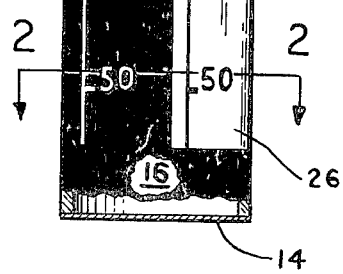
FIG. 1 is a plan view showing the elongated cylinder of the device of the present invention.

In FIGS. 1 and 2 there is shown the elongated cylinder device 10 of the invention. The elongated cylinder 10 made of a translucent material coated mostly black, such as Lucite, and has a hollow interior through which an incident light may pass. The elongated cylinder 10 has a first open end 12 and a second closed end 14. The second closed end 14 is closed off by a reflecting medium, such as aluminum foil, so that the incident light entering via the first open end is reflected back along the hollow interior of the cylinder.

The elongated cylinder 10 has a circumferential wall surface 16. One-half 16' of the wall surface 16 is lined on the interior length thereof with a reflecting medium 18, such as aluminum foil. The reflecting medium 18 is secured to the interior of the wall surface 16' by any conventional method, such as by glueing. The other half 16" of the wall surface 16 is provided with a first scale 20 and a second scale 22. The first scale 20 is a linear scale having a white base line 20', white divisional lines 20", and white reference characters 21 ranging, for example, from 50 to 500. Due to the fact that most of the outer circumferential surface of the wall 16 is coated black, the incident light and the reflected light will pass through the white scale lines and the white reference characters of the first scale so that the first scale is able to be read.

The second scale 22 is similar to the first scale 20 with the difference being that the base line 22', the divisional lines 22", and the reference characters 23 are all black and the outer circumferential portion of the wall 16 in the vicinity of the scale 22 is white, so that the black lines and reference characters will contrast with the white surface, and thereby be easily read. This white field or surface is shown schematically by reference character 26, and is shown as being shaped like a rectangle.

Figure 3:
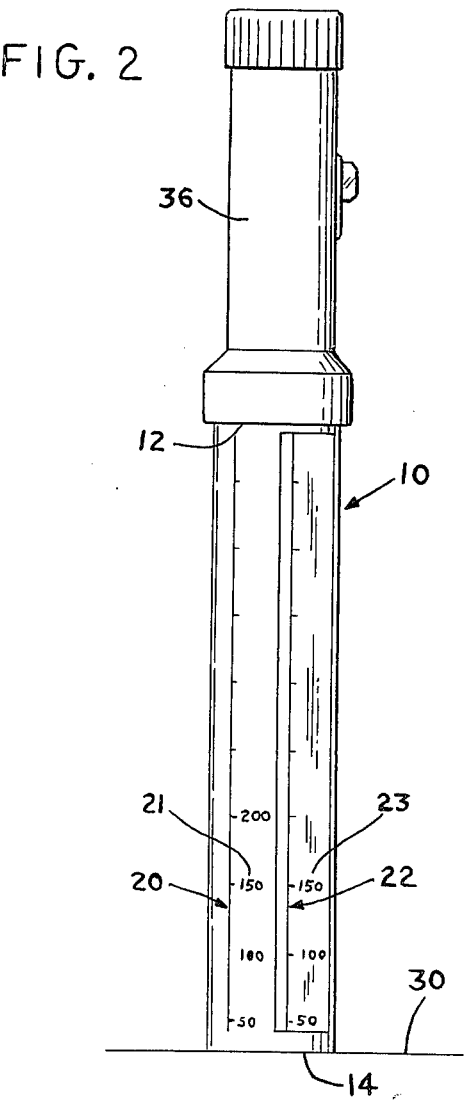
FIG. 3 is a plan view showing the device of the present invention in use on a surface whose gloss is to be measured, where a conventional flashlight is shown resting upon the open end of the elongated cylinder of FIG. 1.

The operation of the device will now be described with the aid of FIG. 3. A surface 30, such as an automobile surface, is desired to be measured as to its relative gloss. The elongated cylinder 10 is placed on the surface 30 so that its closed end 14 rests upon the surface. A flashlight 36, of conventional design, is then placed over the open end 12 and turned on so that an incident light beam is provided. The incident light from the flashlight 36 will be reflected by the reflecting medium on the closed end 24 and by the reflecting medium along the length of the inner wall surface 16' of the circumferential wall 16, and will exit through the wall 16 via the white portions of the wall surface 16'. These white portions, as described above, are the white field 26 for the second scale 22 and the white lines and reference characters of the first scale 20. By viewing the reflection of the elongated cylinder 10 in the surface 30, it may be determined just how polished the surface 30 is. If the surface 30 is a glossy surface, then the reflection of the elongated cylinder will allow for the reading of a relatively high number, such as 450, on at least one of the scales. If the surface is not polished or is relatively unglossy, then only a lower number, such as 150, may be read on at least one of the scales. By using the device of the invention, the ordering of surfaces as to their glossiness may be achieved simply by noting the highest number readable in the reflection of the scales in the surface. It is noted that the reference characters in the two scales 20 and 22 are arranged in ascending order from the closed end 14 to the open end 12.

It is noted that if the surface 30 is black or dark, the reflection of the elongated cylinder 10 will therefore show up the first scale with the white lines and reference characters thereof. If the surface 30 is white or light, then the reflection of the elongated cylinder 10 will show up the second scale with the black lines and black reference characters thereof.

In FIG. 1, the scales 20 and 22 were shown to have reference characters that may be easily read by one viewing the cylinder from the outside. However, since what is important to the present invention is that the reflection of the elongated cylinder in the surface being measured be easily read, it may be provided that the reference characters 21 and 23 of the first and second scales, respectively, be arranged on the wall surface 16" of the wall 16 such that the mirror image of the numerals be shown. Thus, when reading the numbers in the reflection in the surface 16, the actual number will show up, which is the mirror image of the reference characters. Thus, by making the reference characters 21 and 23 the mirror image of the numbers shown, the reflection in the surface 30 will indicate the numbers in the correct, non-mirror image fashion.

While a specific embodiment of the invention has been shown and described, it is to be understood that numerous changes and modifications may be made without departing from the scope and spirit of the invention as defined by the appended claims.

What is claimed is:

1. A device for measuring the glossiness of a surface, such as an automobile surface, comprising: an elongated cylinder having a hollow interior, and a circumferential wall surface, said elongated cylinder having a first open end and a second closed end; reflecting means mounted on the interior portion of said second closed end and on half of the inner circumferential portion of said wall surface; and scale means formed in the other half of said circumferential wall surface, said scale means being translucent in part so as to allow light directed into the interior of said elongated cylinder via said first open end to pass therethrough.

2. The device according to claim 1, wherein said scale means comprises a first scale and a second scale, each of said first and second scales extending in a direction parallel with the longitudinal axis of said elongated cylinder and being in close proximity to each other.

3. The device according to claim 2, wherein each of said first and second scales comprises a base line extending from near said first open end toward said second closed end in a direction parallel with said longitudinal axis of said elongated cylinder, a plurality of divisional lines dividing up said base line into sections, each divisional line being perpendicular to said base line, and a plurality of reference characters for said divisional lines, said reference characters being reference numerals arranged in ascending order such that the lowest of said reference characters is closest to said second closed end of said elongated cylinder and the highest of said reference numerals is closest to said open end of said elongated cylinder.

4. The device according to claim 3, wherein said circumferential wall surface is coated black on most of the outer surface thereof.

5. The device according to claim 4, wherein said base line, said divisional lines, and said reference characters of said first scale are all white to provide the translucence.

6. The device according to claim 4, wherein said base line, said divisional lines, and said reference characters of said second scale are all black, and said outer portion of said circumferential wall surface has in the vicinity of said second scale a white portion to provide translucence.

7. The device according to claim 4, wherein said reference characters of said first and second scales are mirror images of numerals, so that said numerals may be read in the reflection of said elongated cylinder in the surface being measured.

8. The device according to claim 1, in combination with a flashlight, said flashlight having its bulb-end positioned on said first open end of said elongated cylinder to provide the incident light necessary to read the scales in the reflection of the elongated cylinder in the surface to be measured.

* * * * *